US007553158B2

(12) United States Patent
Frider et al.

(10) Patent No.: US 7,553,158 B2
(45) Date of Patent: *Jun. 30, 2009

(54) DENTAL EVACUATION MIRROR

(76) Inventors: Debra Kay Frider, 3602 Westmoor Dr., Moorhead, MN (US) 56560; Paula Ann Wilson, 16750 Seclusion Point Rd., Audubon, MN (US) 56511; Bradley Leo Mauch, 12188 126th Ave., NE., Thief River Falls, MN (US) 56701

( * ) Notice: Subject to any disclaimer, the term of this patent is extended or adjusted under 35 U.S.C. 154(b) by 0 days.

This patent is subject to a terminal disclaimer.

(21) Appl. No.: 11/672,422

(22) Filed: Feb. 7, 2007

(65) Prior Publication Data

US 2007/0148611 A1 Jun. 28, 2007

Related U.S. Application Data

(63) Continuation-in-part of application No. 11/159,442, filed on Jun. 22, 2005, now abandoned, which is a continuation of application No. 10/716,383, filed on Nov. 18, 2003, now Pat. No. 6,932,601.

(51) Int. Cl.
*A61C 3/00* (2006.01)
(52) U.S. Cl. ............................................ 433/31; 433/93
(58) Field of Classification Search .................. 433/30, 433/31, 91, 93
See application file for complete search history.

(56) References Cited

U.S. PATENT DOCUMENTS

| 2,436,040 A | 2/1948 | Friedman |
| 3,052,031 A | 9/1962 | Piscitelli |
| 3,092,910 A | 6/1963 | Warriner |
| 3,102,338 A | 9/1963 | Warriner |
| 3,631,598 A | 1/1972 | Lussier |
| 3,777,756 A | * 12/1973 | Lohr ............................ 433/91 |
| 3,928,916 A | 12/1975 | Hansson |
| 3,969,824 A | 7/1976 | Widen et al. |
| 3,986,266 A | 10/1976 | Vellender |
| 4,511,329 A | 4/1985 | Diamond |
| 4,521,185 A | 6/1985 | Cohen |
| 4,925,391 A | 5/1990 | Berlin |
| D320,075 S | 9/1991 | Berlin |

(Continued)

FOREIGN PATENT DOCUMENTS

DE 19846298 4/2000

(Continued)

*Primary Examiner*—Ralph A Lewis
(74) *Attorney, Agent, or Firm*—Dorsey & Whitney LLP

(57) ABSTRACT

The present invention is a dental evacuation tool for being placed in fluid communication with a dental vacuum. The tool comprises a suction head and an elongated tubular handle. The suction head includes a mirror surface, first and second upward-facing intake orifices adjacent the mirror surface, and an exit fluid pathway that is in fluid communication with the first and second upward-facing intake orifices. The elongated tubular handle includes a first end adapted to be in fluid communication with the vacuum and a second end in fluid communication with the exit fluid pathway. The first and second upward-facing intake orifices are positioned generally opposite each other about the mirror surface, are generally centered about a line that is generally perpendicular to the longitudinal axis of the handle, and open in generally the same direction faced by the mirror.

15 Claims, 11 Drawing Sheets

U.S. PATENT DOCUMENTS

| | | |
|---|---|---|
| 5,078,602 A * | 1/1992 | Honoshofsky ............... 433/91 |
| 5,139,420 A * | 8/1992 | Walker ........................ 433/31 |
| 5,281,134 A | 1/1994 | Schultz |
| 5,295,826 A | 3/1994 | Yandell et al. |
| 5,449,290 A | 9/1995 | Reitz |
| 5,813,856 A | 9/1998 | Lee |
| 5,951,284 A | 9/1999 | Lake |
| 6,247,924 B1 | 6/2001 | Gunnarsson |
| 6,932,601 B2 * | 8/2005 | Frider et al. .................. 433/31 |

FOREIGN PATENT DOCUMENTS

| | | |
|---|---|---|
| DE | 10340278 | 4/2004 |
| EP | 0314657 | 5/1989 |
| FR | 2595939 | 9/1987 |
| FR | 2620930 | 3/1989 |
| FR | 2642298 | 8/1990 |
| JP | 07-136110 | 5/1995 |
| JP | 07-289570 | 11/1995 |
| JP | 10-192309 | 7/1998 |
| SE | 470486 | 5/1994 |
| WO | WO00/12025 | 3/2000 |

\* cited by examiner

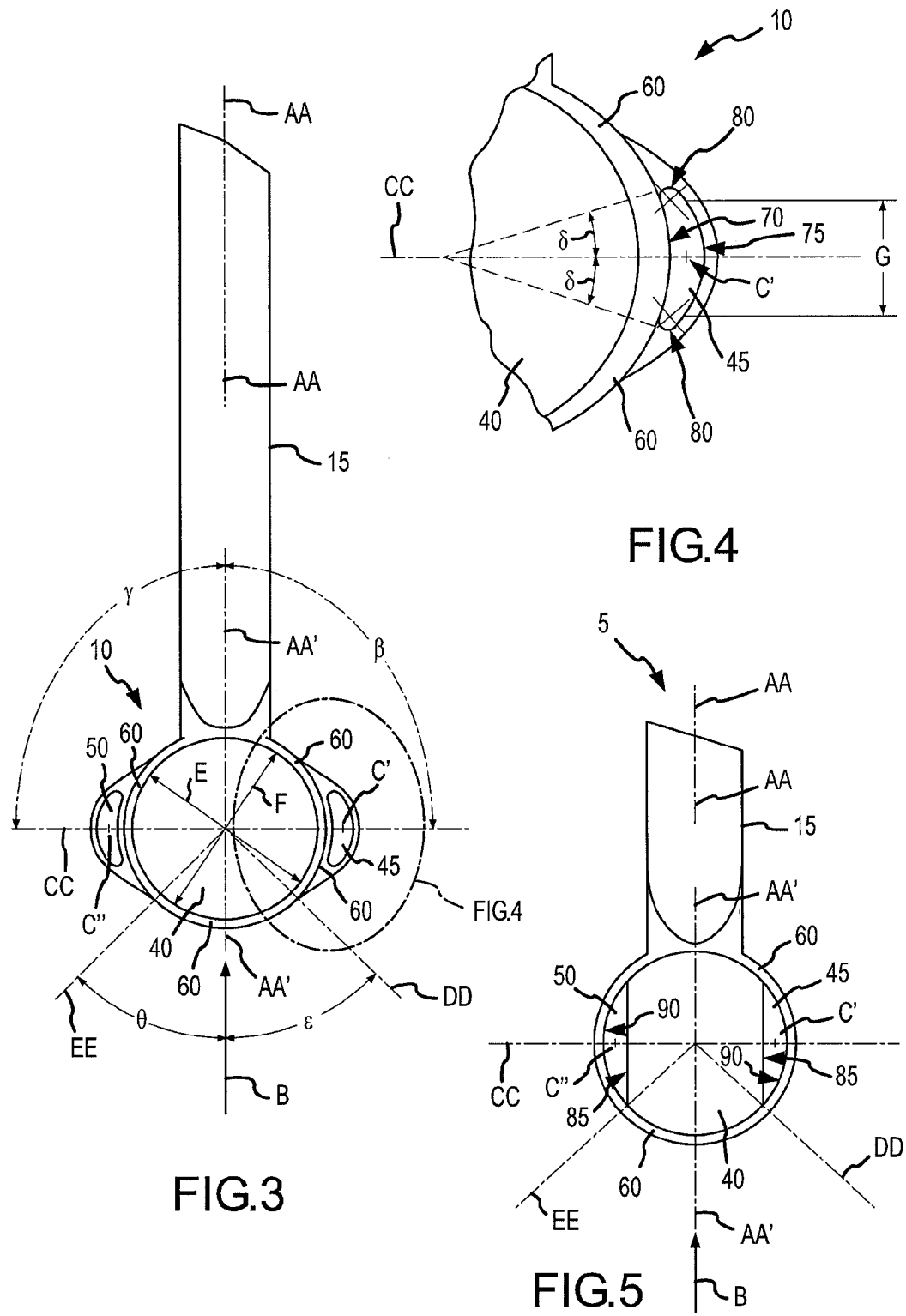

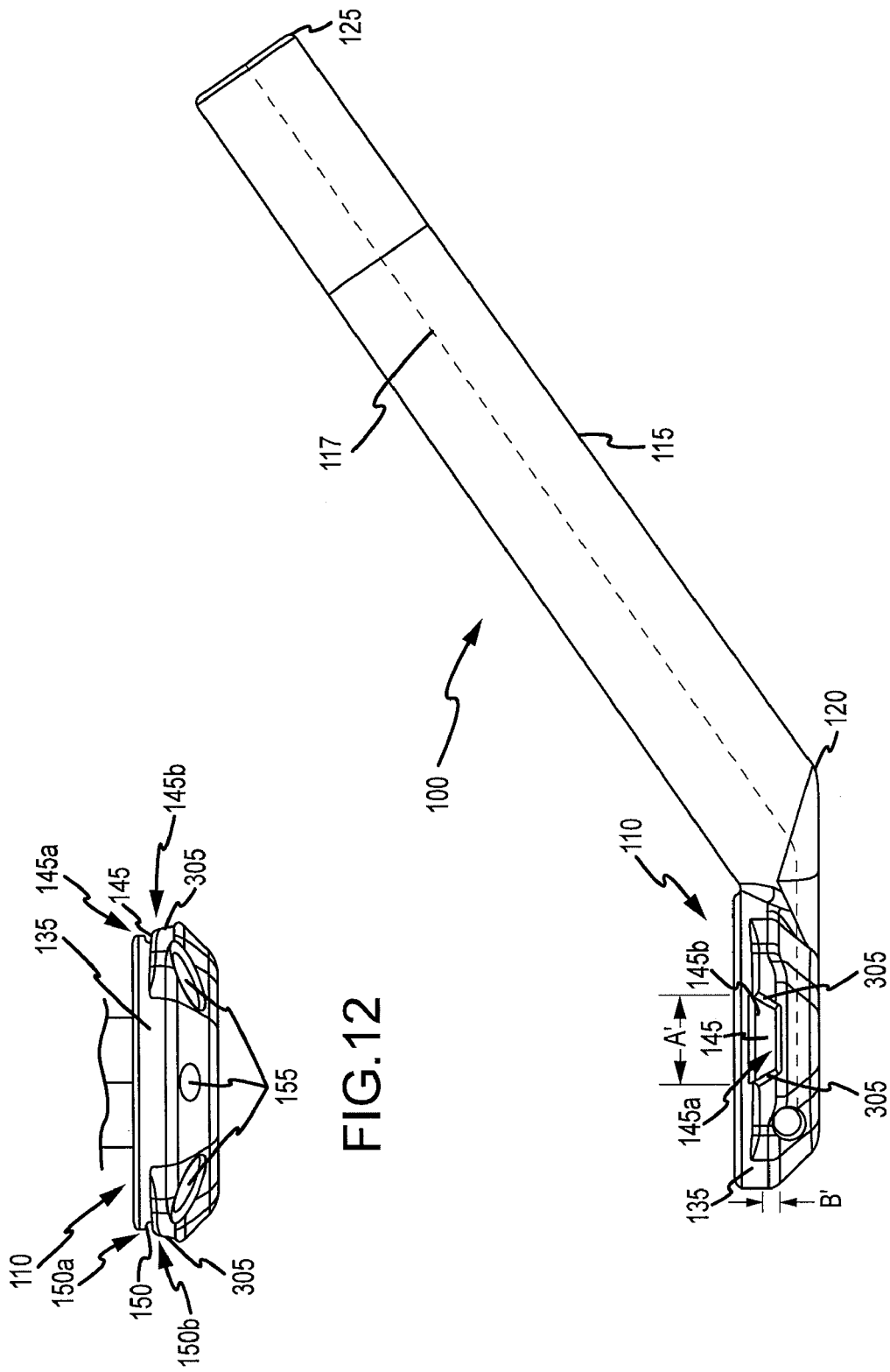

DENTAL EVACUATION MIRROR

CROSS REFERENCE TO RELATED APPLICATIONS

The present application claims priority from, and is a continuation-in-part ("CIP") of U.S. patent application Ser. No. 11/159,442 ("the '442 application"), which was filed Jun. 22, 2005. The '442 application claims priority from, and is a continuation of U.S. patent application Ser. No. 10/716,383 ("the '383 application"), which was filed Nov. 18, 2003. The '383 application issued into U.S. Pat. No. 6,932,601 on Aug. 23, 2005. The aforementioned applications and patent are hereby incorporated by reference in their entireties into the present application.

TECHNICAL FIELD

The present invention relates to dental instruments and methods of making and using dental instruments. More specifically, the present invention relates to dental evacuation mirrors and methods of making and using dental evacuation mirrors.

BACKGROUND OF THE INVENTION

A dental professional will typically sit while performing a dental procedure. To avoid neck strain, the dental professional will utilize a dental mirror to indirectly view the interior of a patient's mouth.

Dental procedures result in the accumulation of liquids and debris within the patient's mouth. A dental professional uses a dental evacuator to vacuum the liquids and debris from the patient's mouth.

Most dental procedures require both a dental mirror and a dental evacuator. Consequently, the features of a dental mirror and a dental evacuator were combined to form prior art dental evacuator mirrors. Unfortunately, the configurations of those prior art devices often cause them to suck in the soft, pliable tissue of a patient's mouth. This is uncomfortable for a patient and impedes the evacuation of fluids and debris. Also, the configurations of the prior art dental evacuator mirrors are such that they require a dental professional to contort their arms excessively to evacuate fluids and debris from a patient's mouth.

There is a need in the art for a dental evacuation mirror that is more comfortable for the patient. Also, there is a need in the art for a dental evacuation mirror that is easier and more comfortable to use for a dental professional.

BRIEF SUMMARY OF THE INVENTION

The present invention, in one embodiment, is a dental evacuation tool for being placed in fluid communication with a dental vacuum. The tool comprises a suction head and an elongated tubular handle. The suction head includes a mirror surface, first and second upward-facing intake orifices adjacent the mirror surface, and an exit fluid pathway that is in fluid communication with the first and second upward-facing intake orifices. The elongated tubular handle includes a first end adapted to be in fluid communication with the vacuum and a second end in fluid communication with the exit fluid pathway. The first and second upward-facing intake orifices are positioned generally opposite each other about the mirror surface, are generally centered about a line that is generally perpendicular to the longitudinal axis of the handle, and open in generally the same direction faced by the mirror.

The present invention, in another embodiment, is a dental evacuation tool for being placed in fluid communication with a dental vacuum. The tool comprises a suction head and an elongated tubular handle. The suction head includes a mirror surface, a first intake orifice adjacent the edge of the mirror surface and having a center point, a second intake orifice adjacent the edge of the mirror surface and having a center point, and an exit fluid pathway that is in fluid communication with the first and second intake orifices. The elongated tubular handle includes a first end adapted to be in fluid communication with the vacuum and a second end in fluid communication with the exit fluid pathway. The center point of the first intake orifice is radially offset by approximately 45 to approximately 135 degrees in a first direction about the edge of the mirror surface from the center of the exit fluid pathway. The center point of the second intake orifice is radially offset by approximately 45 to approximately 135 degrees in a second direction about the edge of the mirror surface from the center of the exit fluid pathway. The first and second intake orifices radially extend by approximately one to approximately 90 degrees away from each side of their respective center points. The first and second intake orifices open in a direction that is approximately zero to approximately 45 degrees from being normal to the mirror surface.

The present invention, in another embodiment, is dental evacuation tool for being placed in fluid communication with a dental vacuum, the tool comprises a suction head including a mirror surface, first and second upward-facing intake orifices adjacent the mirror surface, and an exit fluid pathway that is in fluid communication with the first and second upward-facing intake orifices; and an elongated tubular handle including a first end adapted to be in fluid communication with the vacuum and a second end in fluid communication with the exit fluid pathway. The first and second upward-facing intake orifices are positioned generally opposite each other about the mirror surface and are generally centered about a line that is generally perpendicular to the longitudinal axis of the handle. The first and second upward-facing intake orifices open in generally a same direction faced by the mirror surface and in a generally radial direction relative to a center of the mirror surface.

The present invention, in another embodiment, is a method of making a dental evacuation tool for being placed in fluid communication with a dental vacuum. The method comprises providing a suction head, an elongated tubular handle, and first and second upward-facing intake orifices. The suction head is to include a mirror surface and an exit fluid pathway. The elongated tubular handle is to include a first end in fluid communication with the exit fluid pathway and a second end adapted to be in fluid communication with the vacuum. The first and second upward-facing intake orifices are to be on the suction head adjacent to the mirror surface such that the upward-facing intake orifices are in fluid communication with the exit fluid pathway. Furthermore, the first and second upward-facing intake orifices are to be positioned generally opposite each other about the mirror surface, are to be generally centered about a line that is generally perpendicular to the longitudinal axis of the handle, and are to open in generally the same direction faced by the mirror.

The present invention, in another embodiment, is a method of using a dental evacuation mirror that has a suction head. The suction head has a mirror surface, a backside opposite the mirror surface, and an intake orifice adjacent to the mirror surface. The method comprises placing the suction head in a first position within the mouth of a person and, while maintaining the suction head in the first position, evacuating fluids and/or debris through the intake orifice without suctioning a cheek. The first position is between the cheek and a buccal surface of a tooth, wherein the mirror surface is adjacent to the buccal surface and the backside abuts against and retracts the cheek.

The present invention, in another embodiment, is a method of making a dental evacuation tool for being placed in fluid communication with a dental vacuum. The method comprises providing a suction head, an elongated tubular handle and first and second upward-facing intake orifices. The suction head is to include a mirror surface and an exit fluid pathway. The elongated tubular handle is to include a first end in fluid communication with the exit fluid pathway and a second end adapted to be in fluid communication with the vacuum. The first and second upward-facing intake orifices are to be on the suction head adjacent to the mirror surface such that the upward-facing intake orifices are in fluid communication with the exit fluid pathway. Furthermore, the first and second upward-facing intake orifices are to open in generally a same direction faced by the mirror surface and in a generally radial direction relative to a center of the mirror surface.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3 is a top view of the dental evacuation mirror, wherein the viewing direction is perpendicular to the mirror surface.

FIG. 4 is an enlarged view of the right intake orifice depicted in FIG. 3.

FIG. 5 is a top view of another embodiment of the dental evacuation mirror, wherein the viewing direction is perpendicular to the mirror surface.

FIG. 12 is a partial front view of the dental evacuation mirror of FIG. 10.

FIG. 13 is a side elevation of the dental evacuation mirror of FIG. 10.

DETAILED DESCRIPTION

Figure 1:
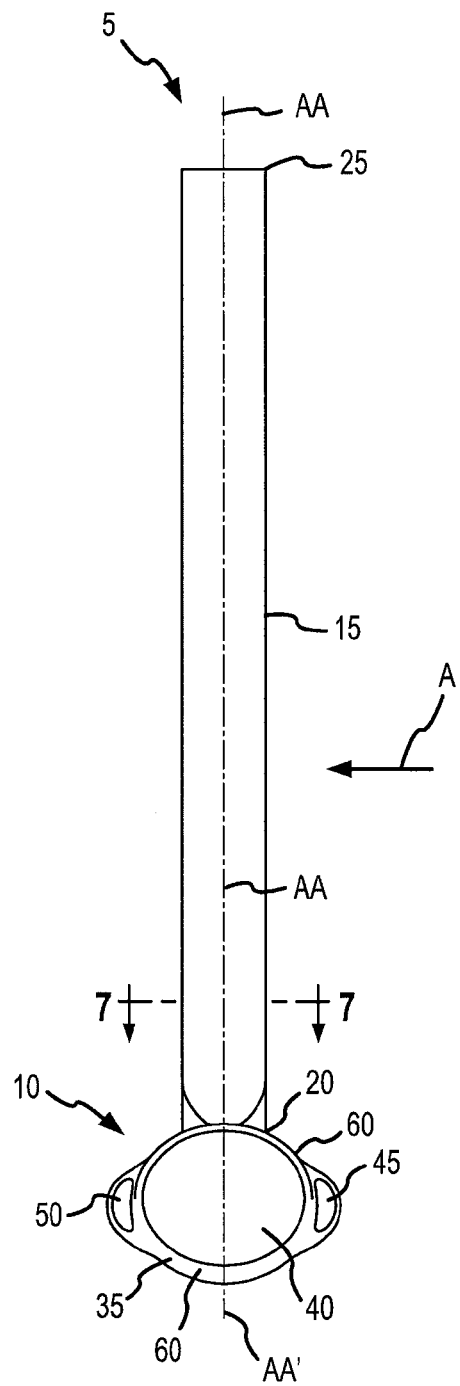
FIG. 1 is a top view of the dental evacuation mirror, wherein the viewing direction is perpendicular to the longitudinal axis of the elongated tubular handle.
Figure 2:
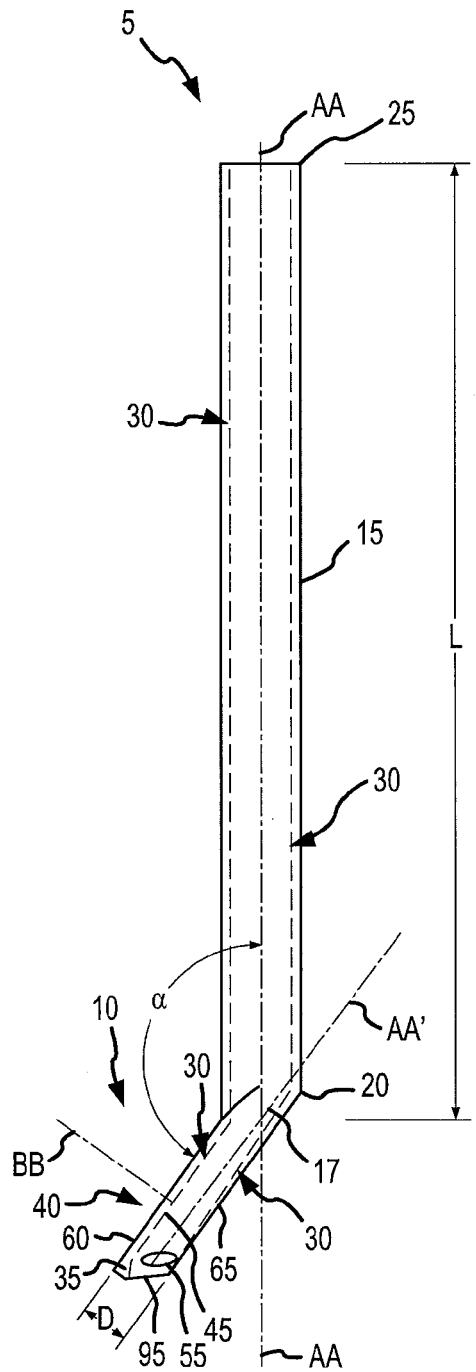
FIG. 2 is a side elevation of the dental evacuation mirror as viewed from the direction of arrow A in FIG. 1.

FIG. 1 is a top view of a dental evacuation mirror 5 including a suction head 10 and an elongated tubular handle 15. In FIG. 1, the dental evacuation mirror 5 is viewed from a direction that is perpendicular to the longitudinal axis AA of the handle 15. FIG. 2 is a side elevation of the dental evacuation mirror 5 as viewed from the direction of arrow A in FIG. 1.

Figure 7:
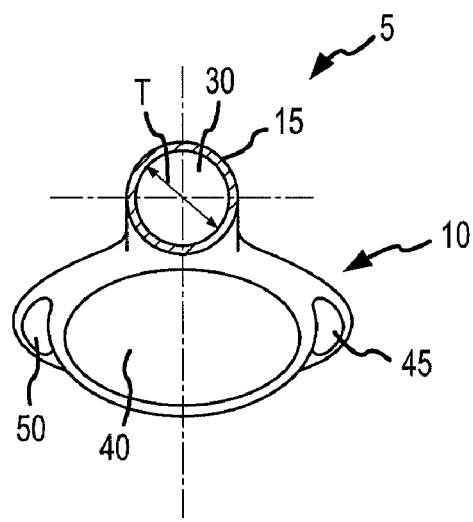
FIG. 7 is a sectional view taken through the elongated tubular handle as shown in FIG. 1.

As shown in FIGS. 1 and 2, the handle 15 has a first end 20 connected to an exit fluid pathway 17 of the suction head 10 and a second end 25 that is adapted to be placed in fluid communication with a dental vacuum. As illustrated in FIG. 2 by phantom lines, the suction head 10 and the handle 15 are hollow in that a void or channel 30 extends from the second end 25, through the length of the handle 15, and into the suction head 10. As indicated in FIG. 7, which is a sectional view taken through the elongated tubular handle 15 as shown in FIG. 1, the void or channel 30 has a diameter T of between approximately 0.25 inches and approximately 0.65 inches. In one embodiment, the diameter T is between approximately 0.35 inches and approximately 0.55 inches. In one embodiment, the diameter T is between approximately 0.40 inches and approximately 0.45 inches. In one embodiment, the diameter T is approximately 0.44 inches.

As shown in FIGS. 1 and 2, the suction head 10 includes a housing 35, a mirror surface 40, a first upward-facing intake orifice 45, a second upward-facing intake orifice 50, and forward-facing intake orifices 55. The housing 35 supports the mirror surface 40 and the orifices 45, 50, 55 are formed in the housing 35. The intake orifices 45, 50, 55 open into the void or channel 30 within the housing 35. Thus, when the dental evacuation mirror 5 is connected to a dental vacuum, the orifices 45, 50, 55 are placed in fluid communication with the dental vacuum via the void or channel 30. The void or channel 30 forms a continuous fluid communication pathway that leads from the orifices 45, 50, 55, through the suction head 10 and the handle 15, and into the dental vacuum.

The suction head 10 and the handle 15 of the dental evacuation mirror 5 may be made of various materials, such as metal, polymer, ceramic, glass, etc., or combinations thereof. Depending on the material, the dental evacuation mirror 5 may be machined, molded, or extruded. The mirror surface 40 may be a metal reflective surface or a non-metal reflective surface such as a glass mirror.

As indicated in FIG. 2, the longitudinal axis AA of the elongated tubular handle 15 forms an angle α with the plane formed by the mirror surface 40. As can be seen in FIGS. 1 and 2, the longitudinal axis AA' of the suction head 10 is parallel to the mirror surface 40 and coplanar with the longitudinal axis AA of the handle 15. Thus, the longitudinal axis AA of the handle 15 will also form angle α with the longitudinal axis AA' of the suction head 10.

In one embodiment the angle α is between approximately 130° and approximately 160°. In one embodiment, the angle α is between approximately 135° and approximately 155°. In one embodiment, the angle α is between approximately 140° and approximately 150°. In one embodiment, the angle α is approximately 145°.

As illustrated in FIG. 2, in one embodiment, the handle 15 has a length L of between approximately 7.5 inches and approximately 4.0 inches. In another embodiment, the handle 15 has a length L of between approximately 7.0 inches and approximately 4.5 inches. In another embodiment, the handle 15 has a length L of between approximately 6.5 inches and approximately 5.0 inches. In another embodiment, the handle 15 has a length L of between approximately 6.0 inches and approximately 5.5 inches.

As shown in FIG. 2, in one embodiment, the top edge 60 of the housing 35 (i.e., the edge of the housing 35 boarding the edge of the mirror surface 40) and the backside 65 of the housing 35 are offset by a distance D of between approximately 0.15 inches and approximately 0.40 inches. In another embodiment, the top edge 60 and the backside 65 are offset by a distance D of between approximately 0.20 inches and approximately 0.35 inches. In another embodiment, the top edge 60 and the backside 65 are offset by a distance D of between approximately 0.25 inches and approximately 0.30 inches. In another embodiment, the top edge 60 and the backside 65 are offset by a distance D of approximately 0.28 inches.

To further describe the features of the suction head 10, reference is now made to FIGS. 3 and 4. FIG. 3 is a top view of the dental evacuation mirror 5, wherein the viewing direction is perpendicular to the mirror surface 40. FIG. 4 is an enlarged view of the first upward-facing intake orifice 45 depicted in FIG. 3.

As shown in FIG. 3, in one embodiment, the first and second upward-facing intake orifices 45, 50 are positioned generally opposite each other about the edge of the mirror surface 40 such that each orifice 45, 50 is generally centered about a line CC that is perpendicular to the axis AA', which is parallel to the mirror surface 40 and coplanar to the longitudinal axis AA of the handle 15. As illustrated in FIG. 3, the upward-facing intake orifices 45, 50 are located in the housing 35 adjacent to the edge of the mirror 40. The upward-facing intake orifices 45, 50 are oriented to open generally in the same direction that the mirror surface 40 is facing. Thus, for the purposes of this specification, "upward-facing" is defined as facing in generally the same direction that the mirror surface 40 is facing.

As shown in FIG. 3, in one embodiment, the upward-facing intake orifices 45, 50 are positioned adjacent to the edge of the mirror surface 40. The center point or centroid C' for the first upward-facing intake orifice 45 is radially offset by angle β about the edge of the mirror surface 40 in a first direction from the axis AA', and the center point or centroid C" for the second upward-facing intake orifice 50 is radially offset by angle γ about the edge of the mirror surface 40 in a second direction from the axis AA'. As indicated in FIG. 4, the upward-facing intake orifices 45, 50 radially extend by angle δ about the edge of the mirror surface 40 from each side of the centroids C', C".

For example, in one embodiment, as indicated in FIG. 3, angles β and γ are each between approximately 45° and approximately 135°. In one embodiment, angles β and γ are each between approximately 50° and approximately 130°. In one embodiment, angles β and γ are each between approximately 55° and approximately 125°. In one embodiment, angles β and γ are each between approximately 60° and approximately 120°. In one embodiment, angles β and γ are each between approximately 65° and approximately 115°. In one embodiment, angles β and γ are each between approximately 70° and approximately 110°. In one embodiment, angles β and γ are each between approximately 75° and approximately 105°. In one embodiment, angles β and γ are each between approximately 80° and approximately 100°. In one embodiment, angles β and γ are each between approximately 85° and approximately 95°. Finally, in one angles β and γ are each approximately 90°.

In one embodiment, as indicated in FIG. 4, angle δ is between approximately 1° and approximately 90°. In one embodiment, angle δ is between approximately 5° and approximately 80°. In one embodiment, angle δ is between approximately 5° and approximately 70°. In one embodiment, angle δ is between approximately 5° and approximately 60°. In one embodiment, angle δ is between approximately 5° and approximately 50°. In one embodiment, angle δ is between approximately 5° and approximately 40°. In one embodiment, angle δ is between approximately 5° and approximately 35°. In one embodiment, angle δ is between approximately 5° and approximately 30°. In one embodiment, angle δ is between approximately 5° and approximately 25°. In one embodiment, angle δ is between approximately 5° and approximately 20°. In one embodiment, angle δ is between approximately 5° and approximately 15°. Finally, in one embodiment, angle δ is between approximately 10° and approximately 15°.

As shown in FIGS. 3 and 4, in one embodiment, the mirror surface 40 has a diameter E of between approximately 0.50 inches and approximately 1.50 inches, and the diameter F of the top edge 60 exceeds the diameter E of the mirror surface 40 by between approximately 0.02 inches and approximately 0.20 inches. For example, as illustrated in FIGS. 3 and 4, the mirror surface 40 has a diameter E of approximately 0.92 inches and the top edge 60 has a diameter F of approximately 1.00 inches. In one embodiment, the mirror surface 40 has a diameter E of between approximately 0.75 inches and approximately 1.25 inches. In one embodiment, the mirror surface 40 has a diameter E of between approximately 0.85 inches and approximately 1.15 inches.

In one embodiment, as illustrated in FIGS. 3 and 4, the housing 35 extends away from the top edge 60 to accommodate the upward-facing intake orifices 45, 50. As shown in FIG. 4, in one embodiment, the perimeters of the upward-facing intake orifices 45, 50 are comprised of an inward radius 70, an outward radius 75, and two end diameters 80. In one embodiment, the inward radius 70 is between approximately 0.25 inches and approximately 0.75 inches, the outward radius 75 is between approximately 0.12 inches and approximately 0.50 inches, and the end diameters 80 are between approximately 0.03 inches and approximately 0.12 inches. In one embodiment, as shown in FIGS. 3 and 4, the inward radius 70 is approximately 0.50 inches, the outward radius 75 is approximately 0.25 inches, the end diameters 80 are approximately 0.06 inches, and the center points used to define the end diameters 80 are separated by distance G, which is 0.30 inches.

To describe the configuration of another embodiment of the suction head 10, reference is now made to FIG. 5. FIG. 5 is a top view of another embodiment of the dental evacuation mirror 5, wherein the viewing direction is perpendicular to the mirror surface 40. As shown in FIG. 5, the housing 35 does not extend from the top edge 60 to accommodate the upward-facing intake orifices 45, 50, and the mirror surface 40 does not fully extend laterally (i.e., in a direction that is perpendicular to axis AA') to the top edge 60 of the housing 35. As illustrated in FIG. 5, the upward-facing intake orifices 45, 50 are located within the boundaries of the top edge 60. The perimeters of the upward-facing intake orifices 45, 50 are formed by the straight edge 85 of the mirror surface 40 intersecting the curved interior edge 90 of the top edge 60.

Figure 6:
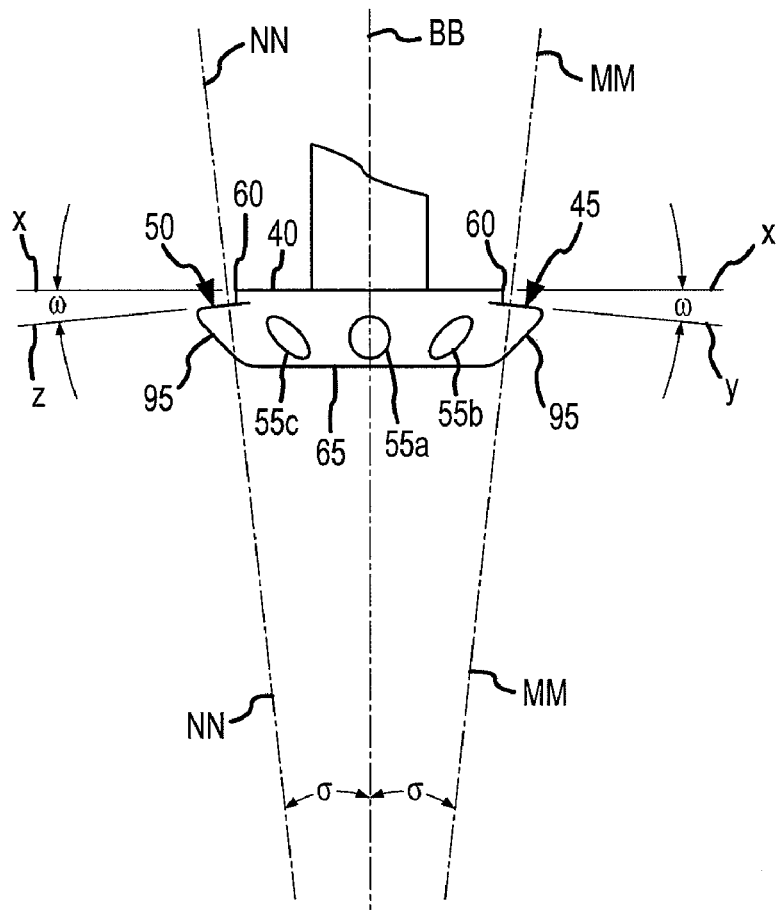
FIG. 6 is an end elevation of the dental evacuation mirror as viewed from the direction of arrow B in FIG. 3.

To further describe the forward-facing intake orifices 55 and the orientation of the upward-facing intake orifices 45, 50, reference in now made to FIGS. 2, 3 and 6. FIG. 6 is an end elevation of the dental evacuation mirror 5 as viewed from the direction of arrow B in FIG. 3.

As shown in FIG. 6, in one embodiment, the housing 35 of the suction head 10 has three forward-facing intake orifices 55. In other embodiments, the housing 35 will have a greater or lesser number of forward-facing intake orifices 55. In one embodiment, the forward-facing intake orifices 55 have a diameter of between approximately 0.05 inches and approximately 0.25 inches. In one embodiment, the forward-facing intake orifices 55 have a diameter of approximately 0.15 inches. For the purpose of this specification, "forward-facing" is defined as facing in a direction that is generally opposite the exit fluid pathway 17 and generally perpendicular to the direction faced by the mirror surface 40.

As illustrated in FIGS. 3 and 6, the center forward-facing intake orifice 55*a* is positioned on axis AA', the right forward-facing intake orifice 55*b* is positioned on axis DD, and the left forward-facing intake orifice 55*c* is positioned on axis EE. Axis AA' forms angle E with axis DD and angle θ with axis EE. In one embodiment, angles ϵ and θ are each between approximately 15° and approximately 60°. In one embodiment, angles ϵ and θ are each between approximately 25° and approximately 55°. In one embodiment, angles ϵ and θ are each between approximately 35° and approximately 50°. In one embodiment, angles ϵ and θ are each between approximately 40° and approximately 50°. In one embodiment, angles ϵ and θ are each approximately 45°.

As illustrated in FIGS. 2 and 6, the housing 35 has sidewalls 95 that extend from the backside 65 to the top edge 60 or from the backside 65 to the edges of the upward-facing orifices 45, 50. As shown in FIGS. 2 and 6, the sidewalls 95 are beveled in that they slope from the backside 65 up and out to the top edge 60 or the edges of the upward-facing orifices 45, 50. In other words, in one embodiment, the angle formed by the backside 65 and the sidewalls 95 is obtuse. In other embodiments, the sidewalls 95 run essentially perpendicular to the mirror surface 40 from the backside 65 up to the top edge 60 or the edges of the upward-facing orifices 45, 50.

As shown in FIG. 6, the upward-facing intake orifices 45, 50 are oriented to face/open generally upward in the same direction faced by the mirror surface 40, which faces upward in the direction of axis BB. As illustrated in FIG. 6, the first upward-facing intake orifice 45 faces/opens generally upward in the direction of axis MM, and the second upward-facing intake orifice 50 faces/opens generally upward in the direction of axis NN. Axis BB forms angle σ with axis MM and axis NN.

In one embodiment, where angle σ is essentially 0° (i.e., axis MM and axis NN are essentially parallel to axis BB), the first and second intake orifices 45, 50 will face/open in a direction that is approximately perpendicular or normal to the mirror surface 40. In one embodiment, where angle σ is between approximately 0° and approximately 45°, the first and second intake orifices 45, 50 will face/open in a direction that is between approximately 0° and approximately 45° from being perpendicular or normal to the mirror surface 40. In one embodiment, where angle σ is between approximately 0° and approximately 35°, the first and second intake orifices 45, 50 will face/open in a direction that is between approximately 0° and approximately 35° from being perpendicular or normal to the mirror surface 40. In one embodiment, where angle σ is between approximately 0° and approximately 25°, the first and second intake orifices 45, 50 will face/open in a direction that is between approximately 0° and approximately 25° from being perpendicular or normal to the mirror surface 40. In one embodiment, where angle σ is between approximately 0° and approximately 15°, the first and second intake orifices 45, 50 will face/open in a direction that is between approximately 0° and approximately 15° from being perpendicular or normal to the mirror surface 40. In one embodiment, where angle σ is between approximately 0° and approximately 10°, the first and second intake orifices 45, 50 will face/open in a direction that is between approximately 0° and approximately 10° from being perpendicular or normal to the mirror surface 40. In one embodiment, where angle σ is approximately 6°, the first and second intake orifices 45, 50 will face/open in a direction that is approximately 6° from being perpendicular or normal to the mirror surface 40.

As illustrated in FIG. 6, the mirror surface rests in plane X, the opening of the upward-facing intake orifice 45 rests in plane Y, and the opening of the upward-facing intake orifice 50 rests in plane Z. Plane X forms an angle ω with planes Y and Z. Plane Y is perpendicular to axis MM and plane Z is perpendicular to axis NN. In one embodiment, as shown in FIG. 6, planes Y and Z are offset back from plane X. In other embodiments, the planes X, Y, and Z are essentially coplanar with each other (i.e., they are not offset from each other).

In one embodiment, where the openings of the upward-facing intake orifices 45, 50 are essentially parallel with the mirror surface 40, the angle ω will be approximately 0°. In other embodiments, where the upward-facing intake orifices 45, 50 are oriented to face generally upward in the same direction faced by the mirror surface 40, but the are not essentially parallel with the mirror surface 40, the angle ω will be between approximately 0° and approximately 45°. In another embodiment, the angle ω will be between approximately 0° and approximately 35°. In another embodiment, the angle ω will be between approximately 0° and approximately 25°. In another embodiment, the angle ω will be between approximately 0° and approximately 15°. In another embodiment, the angle ω will be between approximately 0° and approximately 10°. In another embodiment, the angle ω will be approximately 6°.

Figure 8A:
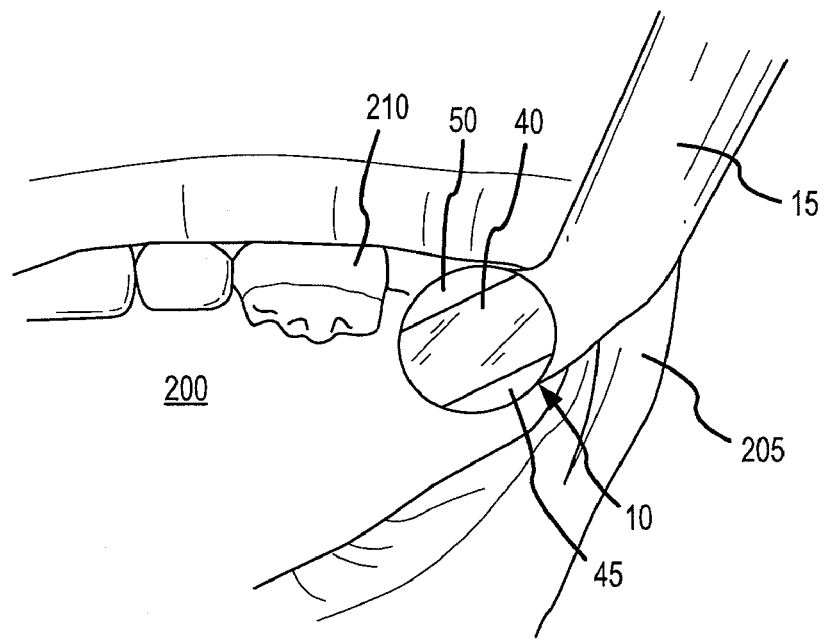
FIG. 8a is a photograph of the dental evacuation mirror being used to view the maxillary, posterior, left quadrant, buccal aspect of a patient's teeth.
Figure 8B:
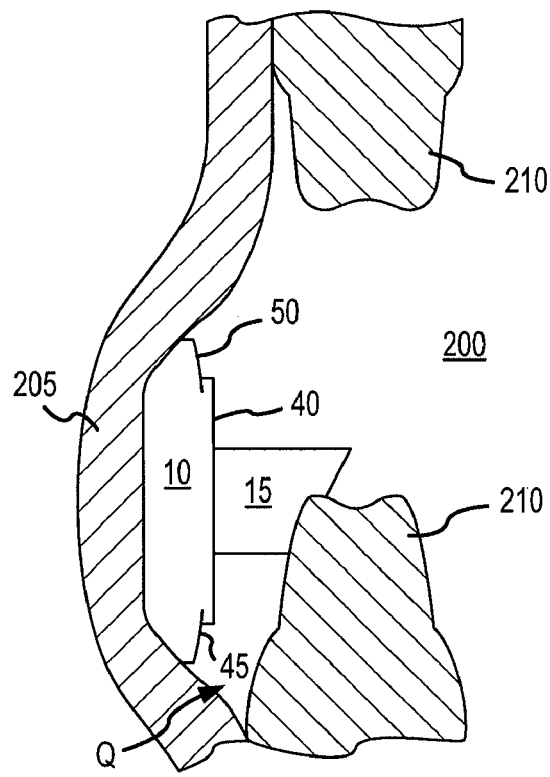
FIG. 8b is a sectional elevation taken through the side of a patient's mouth and showing the dental evacuation mirror retracting the cheek to place the dental evacuation mirror in position to view the mandibular, posterior, left quadrant, buccal aspect of the patient's teeth.
Figure 9A:
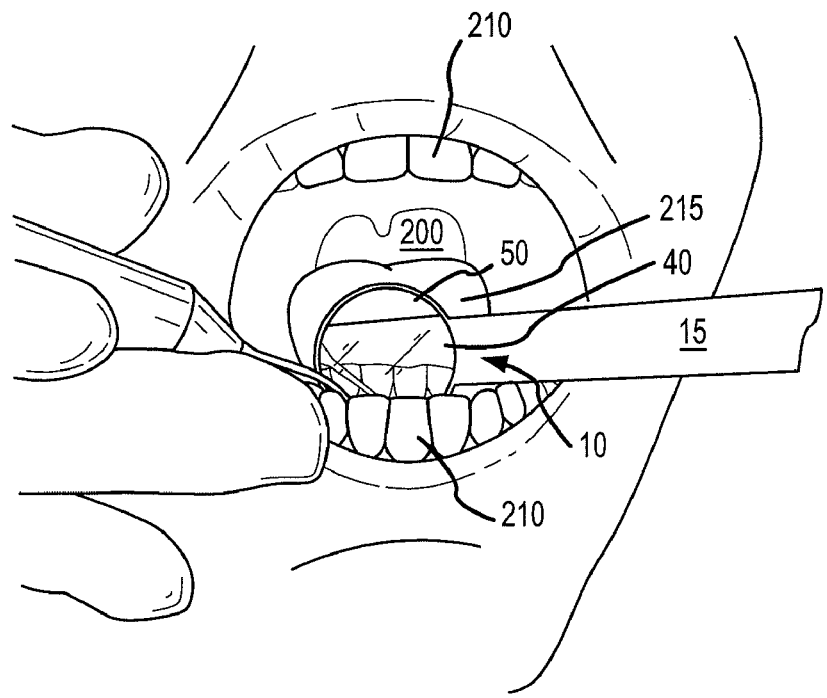
FIG. 9a is a photograph of the dental evacuation mirror being used to view the mandibular, anterior, lingual aspect of a patient's teeth.
Figure 9B:
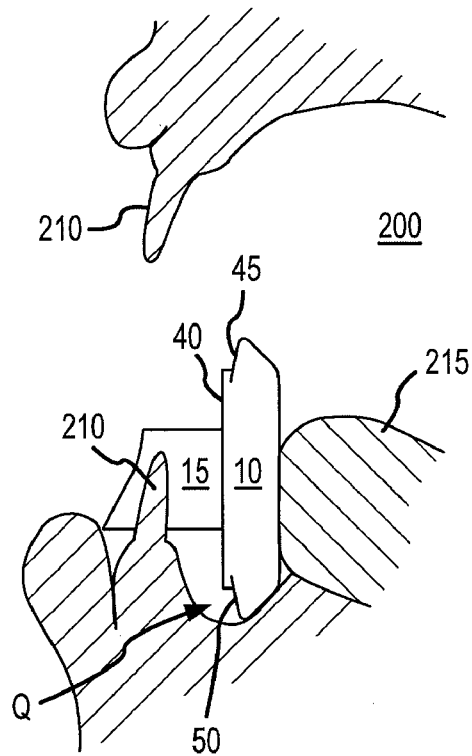
FIG. 9b is a sectional elevation taken through the front of a patient's mouth and showing the dental evacuation mirror retracting the tongue to place the dental evacuation mirror in position to view the mandibular, anterior, lingual aspect of the patient's teeth.

To illustrate some of the benefits of the present invention and to explain its operation, reference is now made to FIGS. 8*a*-9*b*. FIG. 8*a* is a photograph of the dental evacuation mirror 5 being used to view the maxillary, posterior, left quadrant, buccal aspect of a patient's teeth. FIG. 8*b* is a sectional elevation taken through the side of a patient's mouth 200 and showing the dental evacuation mirror 5 retracting the cheek 205 to place the dental evacuation mirror 5 in position to view the mandibular, posterior, left quadrant, buccal aspect of the patient's teeth 210. FIG. 9*a* is a photograph of the dental evacuation mirror 5 being used to view the mandibular, anterior, lingual aspect of a patient's teeth. FIG. 9*b* is a sectional elevation taken through the front of a patient's mouth 200 and showing the dental evacuation mirror 5 retracting the tongue 215 to place the dental evacuation mirror 5 in position to view the mandibular, anterior, lingual aspect of the patient's teeth 210.

When the dental evacuation mirror 5 is utilized, the end 25 of the handle 15 may be placed in fluid communication with a dental vacuum. A dental professional then holds the handle 15 of the dental evacuation mirror 5 and guides the suction head 10 into position inside the patient's mouth 200, as indicated in FIGS. 8a and 9a.

As shown in FIGS. 8a-9b, the suction head 10 may be positioned/oriented so the mirror surface 40 is facing the item (e.g., a tooth 210) being indirectly viewed via the mirror surface 40. If there is soft tissue (e.g., a cheek 205 or tongue 215) immediately adjacent to the item being viewed, the backside 65 of the housing 35 may be used to retract the soft tissue to provide adequate clearance between the mirror surface 40 and the item being viewed. Simultaneously, the intake orifices 45, 50, 55 may be used to evacuate liquids and debris that accumulate in the mouth during a dental procedure.

As shown in FIG. 8b, because of the configuration of the suction head 10 and the orientation of the upward-facing orifices 45, 50, the dental evacuation mirror 5 is able to retract the cheek 205 to view the buccal aspect of the teeth 210 without suctioning the soft tissue of the cheek 205 with the upward-facing orifices 45, 50. Thus, the upward-facing orifices 45, 50 are not obstructed by the cheek 205, which makes the dental evacuation mirror 5 more comfortable for the patient and more efficient at removing liquids and debris.

As shown in FIG. 9b, because of the configuration of the suction head 10 and the orientation of the upward-facing orifices 45, 50, the dental evacuation mirror 5 is able to retract the tongue 215 to view the lingual aspect of the teeth 210 without suctioning the soft tissue of the tongue 215 (or the soft tissue under the tongue 215) with the upward-facing orifices 45, 50. Thus, the upward-facing orifices 45, 50 are not obstructed by the tongue 215, which makes the dental evacuation mirror 5 more comfortable for the patient and more efficient at removing liquids and debris.

During dental procedures, fluids and debris tend to accumulate in the low spots and crevices of the mouth that are adjacent to the area of the mouth undergoing the procedure (e.g., areas Q in FIGS. 8b and 9b). As indicated in FIGS. 8b and 9b, because of the configuration of the dental evacuation mirror 5, the upward-facing intake orifices 45, 50 are ideally positioned/oriented to evacuate the low spots and crevices (areas Q) without suctioning the surrounding soft tissues 205, 215 or requiring the dental professional to contort his arm excessively to access the fluids and debris in those areas Q.

Figure 10:
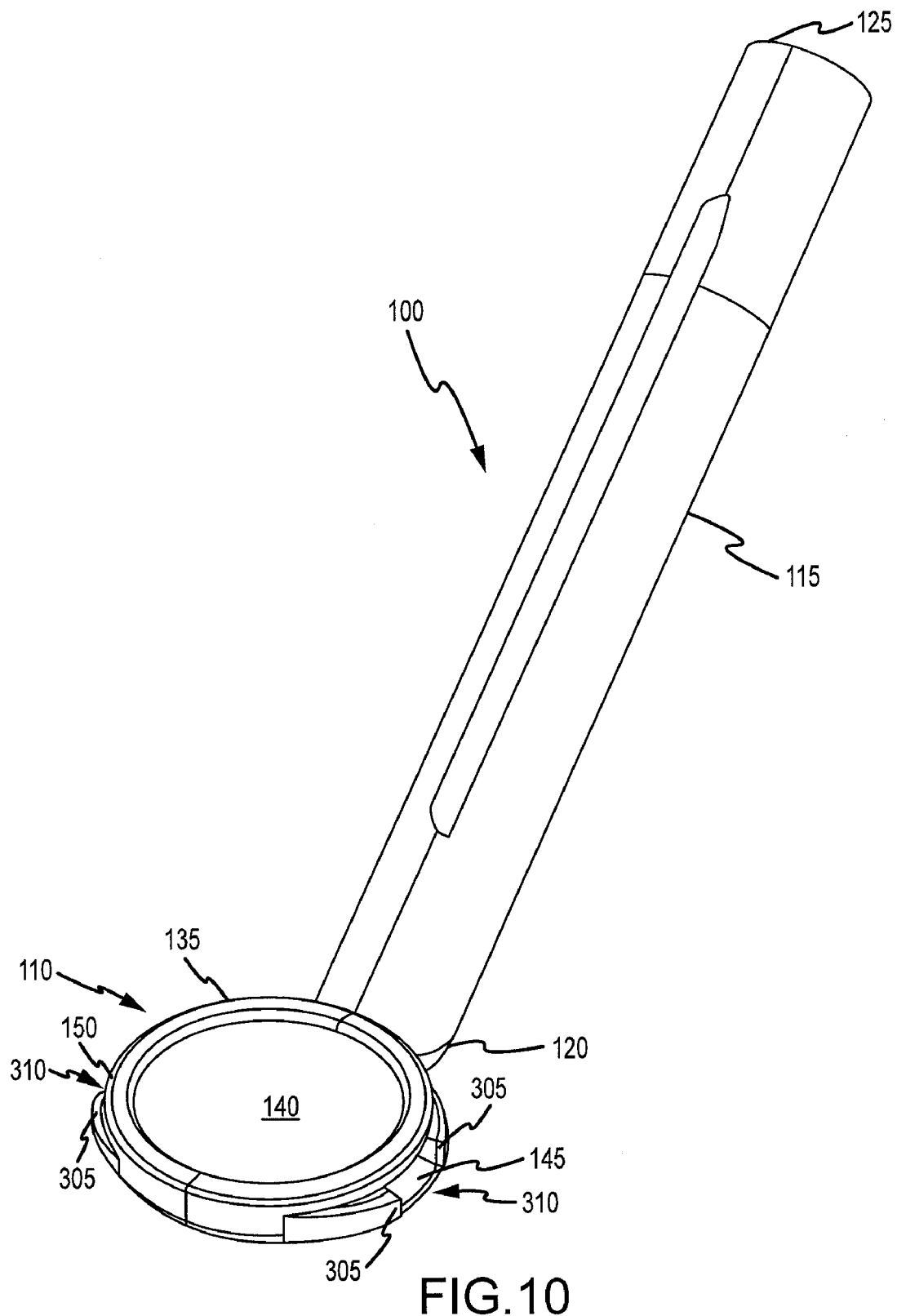
FIG. 10 is a perspective view of another embodiment of the dental evacuation mirror.
Figure 11:
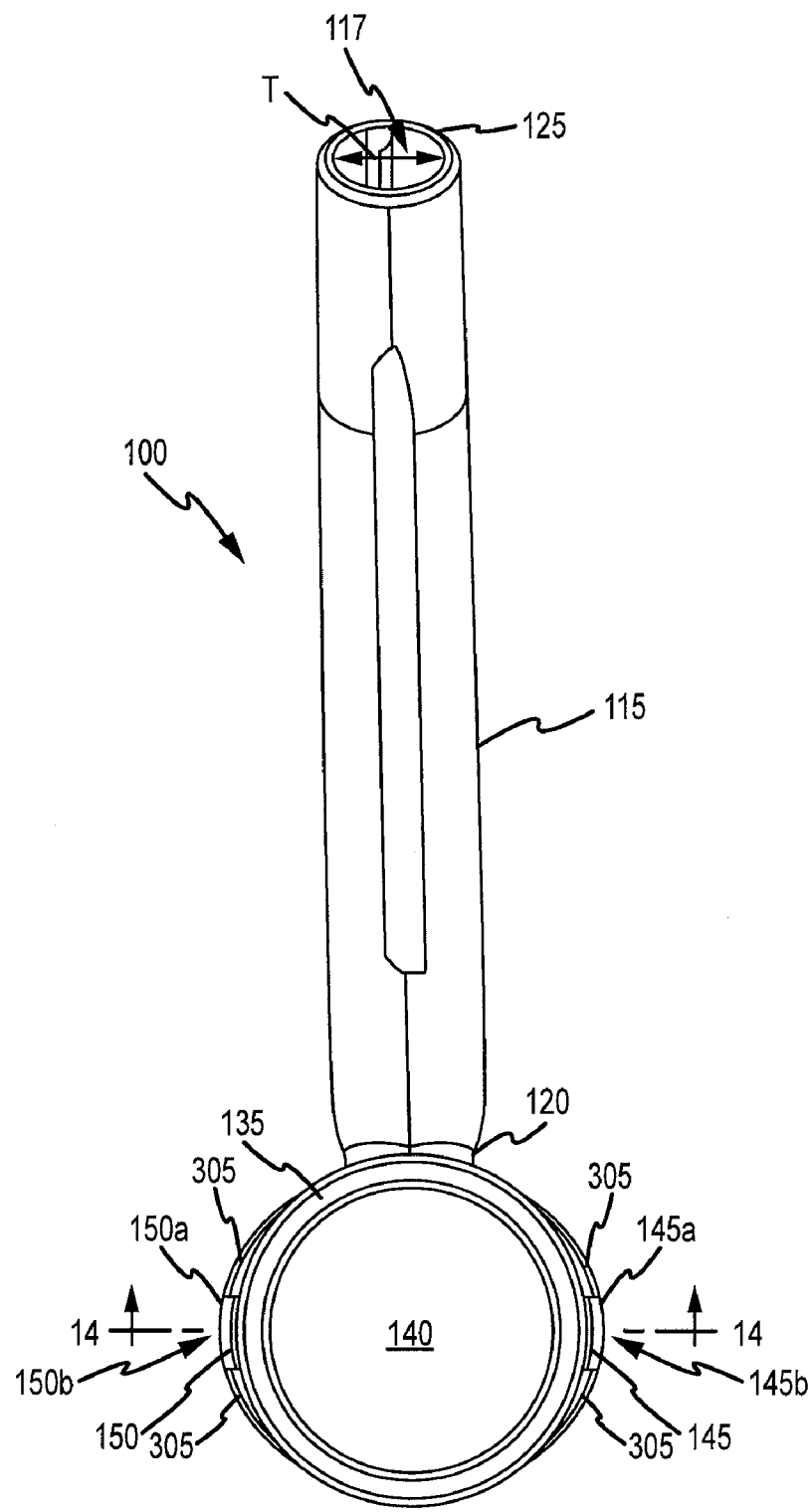
FIG. 11 is a top view of the dental evacuation mirror of FIG. 10, wherein the viewing direction is perpendicular to the mirror surface.
Figure 14:
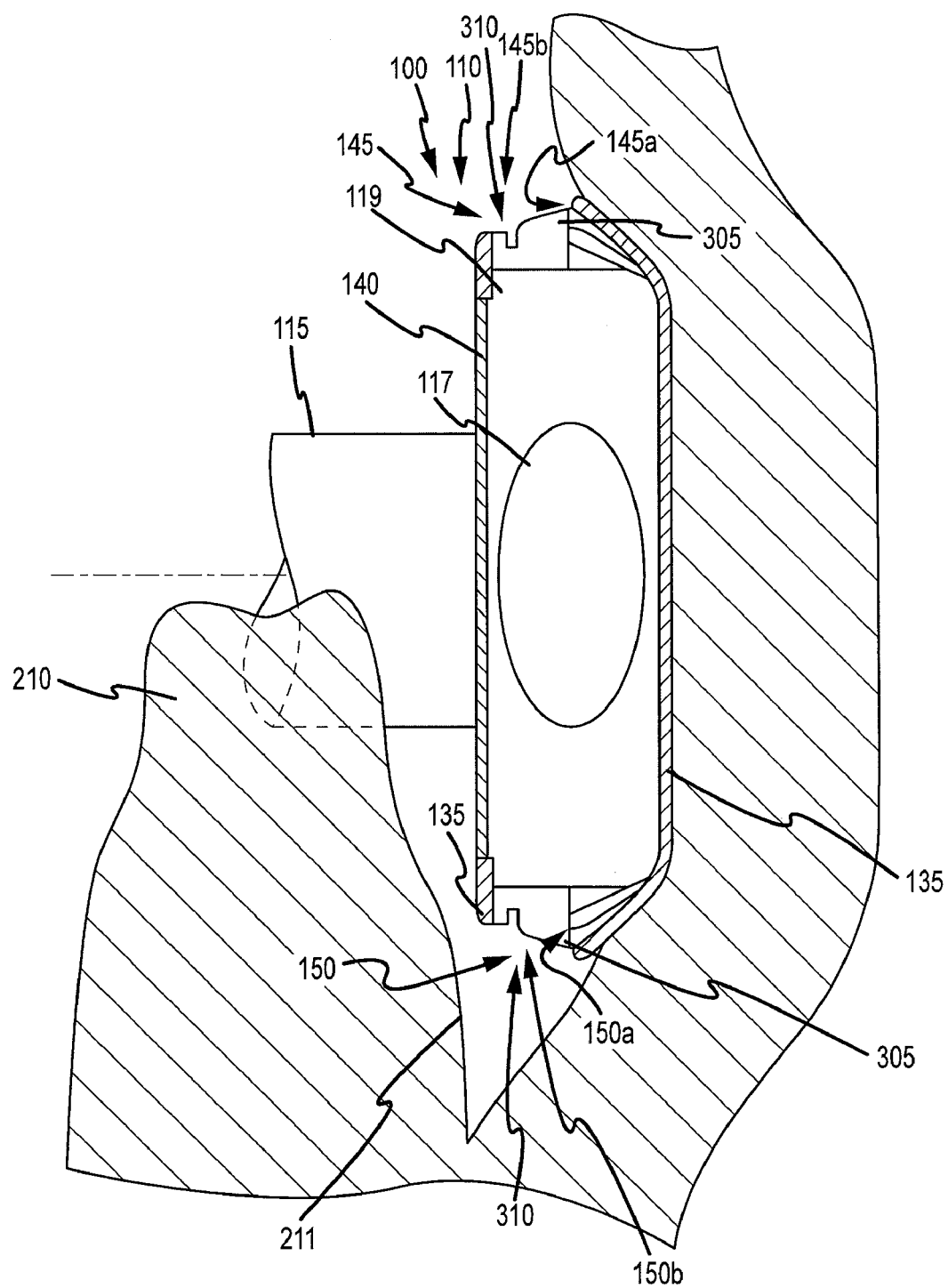
FIG. 14 is a sectional elevation taken through the side of a patient's mouth and the dental evacuation mirror as viewed along section line 14-14 of FIG. 11, wherein the dental evacuation mirror is retracting the cheek to place the dental evacuation mirror in position to view the mandibular, posterior, left quadrant, buccal aspect of the patient's teeth.

FIG. 10 is a perspective view of another embodiment of the dental evacuation mirror 100 including a suction head 110 and an elongated tubular handle 115. FIG. 11 is a top view of the dental evacuation mirror 100, in which the dental evacuation mirror 100 is viewed from a direction that is perpendicular to a mirror surface 40 of the dental evacuation mirror 100. FIG. 12 is a partial front view of the dental evacuation mirror 100, and FIG. 13 a side elevation of the dental evacuation mirror 100. FIG. 14 is a sectional elevation taken through the side of a patient's mouth and the dental evacuation mirror 100 as viewed along section line 14-14 of FIG. 11, wherein the dental evacuation mirror 100 is retracting the cheek 205 to place the dental evacuation mirror 100 in position to view the mandibular, posterior, left quadrant, buccal aspect of the patient's teeth 210.

As shown in FIGS. 10, 11 and 13, the handle 115 has a first end 120 connected to an exit fluid pathway 117 of the suction head 110 and a second end 125 that is adapted to be placed in fluid communication with a dental vacuum. As can be understood from FIGS. 11, 13 and 14, the suction head 110 and the handle 115 are hollow in that a void or channel 117 extends from the second end 125, through the length of the handle 115, and into the void 119 of the suction head 110, as described above with respect to FIGS. 1, 2 and 7.

As indicated in FIG. 13, the void or channel 117 may include a diameter T of between approximately 0.25 inches and approximately 0.65 inches. In one embodiment, the diameter T is between approximately 0.35 inches and approximately 0.55 inches. In one embodiment, the diameter T is between approximately 0.40 inches and approximately 0.45 inches. In one embodiment, the diameter T is approximately 0.41 inches.

As shown in FIGS. 10, 11 and 13, the suction head 110 includes a housing 135, the mirror surface 140, a first upward-facing intake orifice 145, and a second upward-facing intake orifice 150. As a comparison of FIGS. 3 and 11 reveal, the upward facing intake orifices 145, 150 of the embodiment depicted in FIG. 11 are closer to an outer circumferential profile of the suction head 10 than the upward facing intake orifices 45, 50 of the embodiment depicted in FIG. 3. The closeness of the upward facing intake orifices 145, 150 to the suction head outer circumferential profile reduces the size of the suction head 110, which may improve maneuverability within a patient's mouth.

In a manner similar to the upward facing orifices 45, 50 of the embodiment depicted in FIGS. 1-9, the upward facing intake orifices 145, 150 of the embodiment depicted in FIGS. 10-14 also open in generally the same direction faced by the mirror surface 140. Thus, as shown in FIG. 14, because of the configuration of the suction head 110 and the orientation of the upward-facing orifices 145, 510, the dental evacuation mirror 100 is able to retract the cheek 205 to view the buccal aspect of the teeth 210 without suctioning the soft tissue of the cheek 205 with the upward-facing orifices 45, 50. Thus, the upward-facing orifices 145, 150 are not obstructed by the cheek 205, which makes the dental evacuation mirror 100 more comfortable for the patient and more efficient at removing liquids and debris.

As shown in FIG. 11, in one embodiment, the upward facing intake orifices 145, 150, or at least their upward facing portions 145a, 150a, may be non-circular. Specifically, in one embodiment, the orifices 145, 150, or at least their upward facing portions 145a, 150a, are slot-like with lengths substantially longer than their widths. Their lengths extend along a route that is adjacent to, and generally matches, the periphery of the mirror 140.

As indicated in FIGS. 10-16, in one embodiment, the upward facing orifices 145, 150 are located within recesses 310 defined in the housing 135. In one embodiment as depicted in FIG. 13, the recesses 310 may each define a notched opening that includes a width A' and a depth B'. In one embodiment, the maximum depth may be less than half the maximum width. Further, in one embodiment, the openings defined by the recesses 145, 150 may decrease in width in a downward direction, i.e., opposite the mirror surface facing direction. In one embodiment, where the upward facing orifices 145, 150 include upward facing portions 145a, 150a and radially outward facing portions 145b, 150b, the orifices 145, 150 may have dimensions corresponding to the recesses 310 such that the orifices 145, 150 have widths A' and depths B' as discussed above.

In one embodiment, the notched configuration of the orifices 145, 150 and/or recesses 310 assists in molding the suction head 110. For example, the notched configuration may assist in releasing the suction head 110 from the mold. The notched configuration may offer other advantages as provided below.

As can be understood from a comparison of FIGS. 3 and 14, for one version of the embodiment illustrated in FIGS. 10-14 and as a result of the notched configuration of the orifices 145, 150, the upward facing orifices 145, 150 are perpendicularly offset from the mirror surface 140 a greater distance than the upward facing orifices 45, 50 of the embodiment illustrated in FIG. 3. As a result of the notched configuration and/or the upward facing orifices 145, 150 being perpendicularly offset from the mirror surface 140 a greater distance, and as can be understood from FIGS. 11-14, in one embodiment the upward facing intake orifices 145, 150 include upward facing portions 145a, 145b that extend or transition into radially outward facing portions 145b, 150b.

The upward facing portions 145a, 150a face upward in generally the same direction as the mirror surface 140, and the radially outward facing portions 145b, 150b face in a generally radially outward direction relative to a center of the mirror surface 140, for example, radially outward away from the radial edge of the mirror surface 140. As can be understood from FIG. 14, in one embodiment, the increased offset between the mirror surface 140 and the upward facing portions 145a, 150a of the orifices 145, 150 increases the distance between the orifices 145, 150 and the gum surface 211 from which the tooth 210 extends, thereby reducing the likelihood the gum surface 211 will block the suction action of the orifices 145, 150. As can be understood FIG. 14, in embodiments of the upward facing orifices 145, 150 with upward facing portions 145a, 150a extending or transitioning into radially outward facing portions 145b, 150b, the radially outward facing portions 145b, 150b increase the orifice area available for the passage of debris into the suction head void 119.

Figure 15:
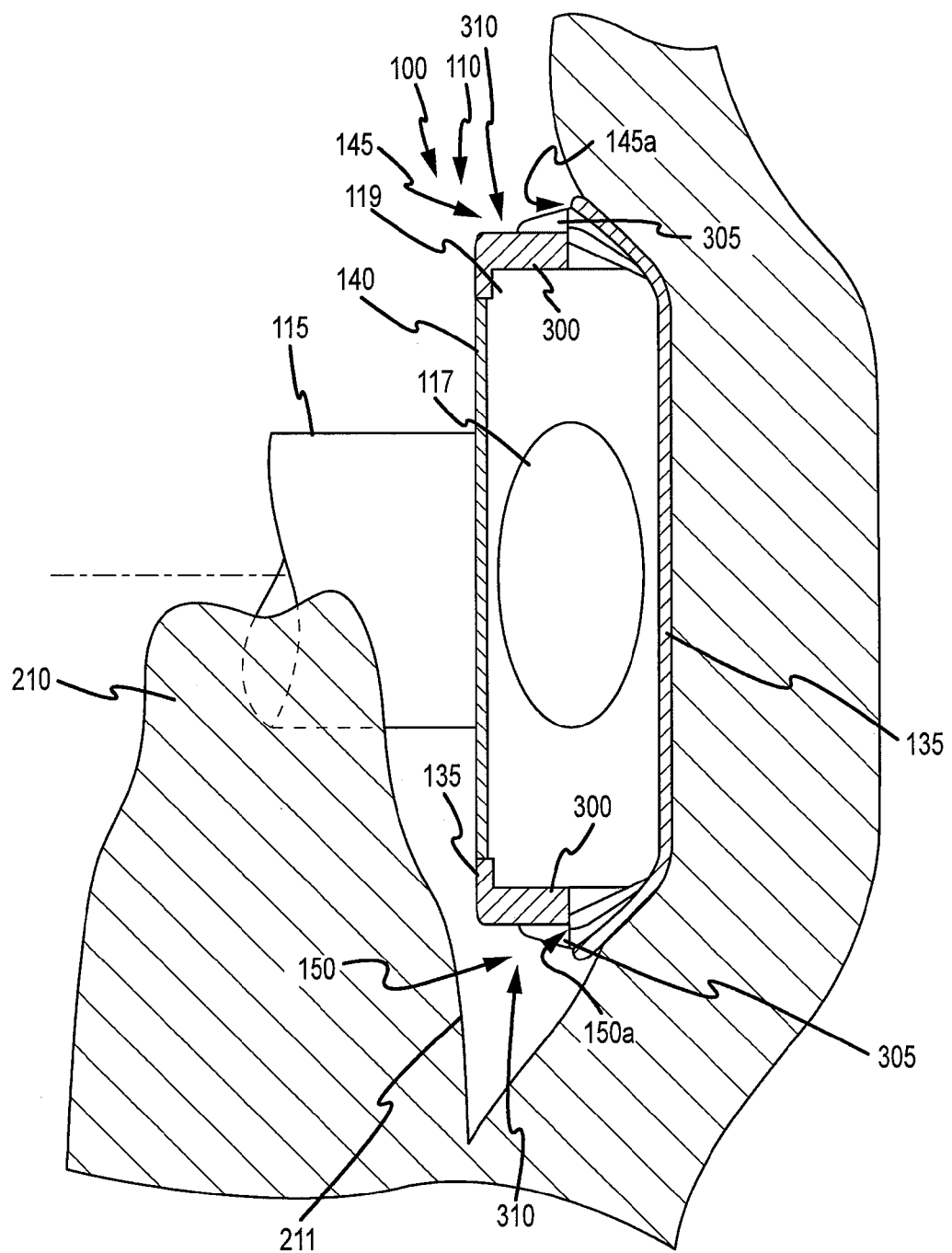
FIG. 15 is the same view as depicted in FIG. 14, except of an alternative orifice configuration wherein the notched or offset upward facing orifices have upward facing portions that are offset substantially rearward from the mirror surface, but do not have radially outward opening portions on account of a lip or rim that extends rearward from the mirror.
Figure 16:
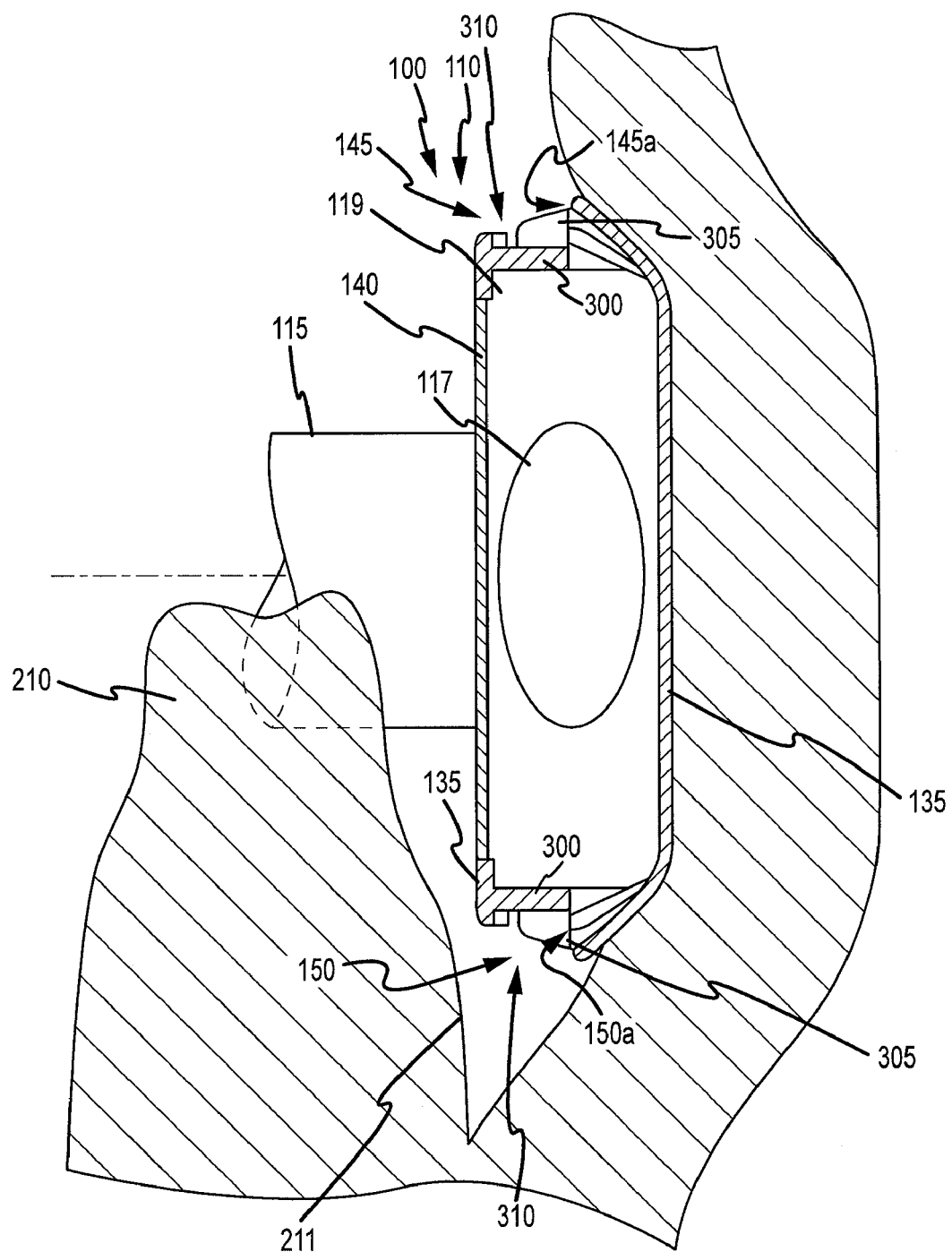
FIG. 16 is the same view depicted in FIG. 15, except the lip is configured differently.

While the presence of radially outward facing portions 145b, 150b may provide additional orifice area for the passage of debris, it should be noted that the radially outward facing portions 145b, 150b are not necessary for the functional operation of upward facing orifices 145, 150 having a reduced profile, as most clearly illustrated in FIG. 11, and/or a notched or rearward offset configuration, as most clearly illustrated FIG. 13. For example, in FIGS. 15 and 16, which are the same views as depicted in FIG. 14, except of alternative orifice configurations, the notched or offset upward facing orifices 145, 150 have upward facing portions 145a, 150a that are offset substantially rearward from the mirror surface 140, but do not have radially outward opening portions 145b, 150b on account of a lip or rim 300 of the housing 135 that extends rearward from the mirror 140. Thus, in some embodiments, as depicted in FIGS. 15 and 16, a rim 300 of the housing extends into each recess 310 containing an upward facing orifice 145, 150 to form a back wall 300 of the recess 310. The back wall 300 of the recess 310 closes off an avenue in which a radially outward portion 145b, 150b of an orifice 145, 150 could be formed.

As can be understood from FIGS. 10 and 14-16, in one embodiment, the circumferentially extending housing 135 adjacent the orifices 145, 150 forms rims or edges 305 that define a recess 310 in the housing 135 in which the orifices 145, 150 reside. The edges 305 and the recess 310 assist in maintaining oral tissue 205, 211, 215 an adequate distance from the upward facing orifices 145, 150, thereby assisting in preventing oral tissue from occluding the orifices 145, 150. As depicted in FIGS. 14-16, in one embodiment, regardless of whether the upward facing orifices 145, 150 include radially outward facing portions 145b, 150b or not, the recess 310 containing each orifice 145, 150 faces generally radially outward away from the radial edge of the mirror 140.

As shown in FIGS. 12 and 13, the suction head 110 also includes forward-facing intake orifices 155. The housing 135 supports the mirror surface 140 and the orifices 145, 150, 155 are formed in the housing 135. The intake orifices 145, 150, 155 open into the suction head void 119 defined by the housing 135 and which is in fluid communication with the channel 117 extending through the handle 115. Thus, when the dental evacuation mirror 100 is connected to a dental vacuum, the orifices 145, 150, 155 are placed in fluid communication with the dental vacuum via the void and channel. The void and channel forms a continuous fluid communication pathway that leads from the orifices 145, 150, 155, through the suction head 110 and the handle 115, and into the dental vacuum.

As discussed above, the suction head 110 and the handle 115 of the dental evacuation mirror 100 may be made of various materials, such as metal, polymer, ceramic, glass, etc., or combinations thereof. Depending on the material, the dental evacuation mirror 100 may be machined, molded, or extruded. The mirror surface 140 may be a metal reflective surface or a non-metal reflective surface such as a glass mirror.

Various features of the embodiment described above with respect to FIGS. 1-7 may be incorporated into the embodiment of FIGS. 11-13. Such features, such as the angle that the elongated tubular handle 115 forms with the plane formed by the mirror surface 140 and the suction head 110 are not detailed for the sake of simplicity.

The handle 115 may have a length L of between approximately 3.5 inches and approximately 3.0 inches. This may improve handling of the dental evacuation mirror 100. In particular, this may reduce a relatively non-flexible length of the dental evacuation mirror 100 which may be attached to a relatively flexible hose to connect to the dental vacuum.

As shown in FIG. 11, in one embodiment, the first and second upward-facing intake orifices 145, 150 are positioned generally opposite each other about the edge of the mirror surface 140 such that each orifice 145, 150 is generally centered as in the embodiment of FIGS. 1-7. The upward-facing intake orifices 145, 150 are located in the housing 135 adjacent to the edge of the mirror 140. The upward-facing intake orifices 145, 150 are oriented to open generally in the same direction that the mirror surface 140 is facing. In one embodiment, the upward facing intake orifices 145, 150 will also have portions 145b, 150b that face radially outward in addition to portions 145a, 150a that face upward in generally the same direction as the mirror. Thus, although "upward-facing" is previously defined as facing in generally the same direction that the mirror surface is facing, this is not meant to exclude the upward-facing intake orifices 145, 150 from extending into or having portions opening in an additional direction, which, for example, may be radially outward.

As shown in FIG. 11, in one embodiment, the upward-facing intake orifices 145, 150 are positioned adjacent to the edge of the mirror surface 140. The center point or centroid for the first and second upward-facing intake orifices 145, 150 may be radially offset and may radially extend as in the embodiment of FIGS. 1-7.

Although the present invention has been described with reference to preferred embodiments, persons skilled in the art will recognize that changes may be made in form and detail without departing from the spirit and scope of the invention.

We claim:

1. A dental evacuation tool for being placed in fluid communication with a dental vacuum, the tool comprising:

a suction head;

a handle extending from the suction head; and a fluid conveying pathway extending through the suction head and handle, wherein the suction head includes:

a housing;

a mirror surface supported by the housing;

a first shelf protruding laterally from the housing and having a top surface offset rearward from the mirror surface, a side surface near to and generally following an outer circumferential profile of the suction head, and a bottom surface having a beveled shape as it extends between the side surface and the housing, wherein the side surface has a height measured in a direction generally the same as a direction faced by the mirror;

a first recess in the top surface of the first shelf, the first recess having a bottom defined by a depth approximately equal to the height of the side surface of the first shelf, the first recess further defined by a first edge proximal to the handle and a second edge distal to the handle, the recess extending laterally through the housing, into the fluid conveying pathway, and defining a radially outward facing portion, the first recess generally centered about a line extending across the suction head generally transverse to a longitudinally extending axis of the handle;

a first upward-facing intake orifice extending through the bottom of the first recess, along an interior surface of the bevel shaped bottom surface of the first shelf, and into the fluid conveying pathway, wherein the first upward-facing intake orifice opens in a direction substantially the same as a direction faced by the mirror surface; and at least one forward-facing intake orifice.

2. The tool of claim 1, wherein the first upward-facing intake orifice has a length substantially greater than a width of the first upward-facing intake orifice.

3. The tool of claim 1, wherein the forward-facing intake orifice is in fluid communication with the fluid conveying pathway and is positioned on the suction head generally opposite the handle.

4. The tool of claim 3, wherein the forward-facing intake orifice opens in a direction that is generally perpendicular to the direction faced by the mirror surface.

5. The tool of claim 3, wherein the forward-facing intake orifice opens in a direction that is generally opposite the direction faced by the mirror surface.

6. The tool of claim 1, wherein the suction head further includes a sidewall and a backside that is generally opposite the mirror surface wherein the at least one forward-facing intake orifice is located in the sidewall generally opposite the handle.

7. The tool of claim 6, wherein the backside and the sidewall form an obtuse angle.

8. The tool of claim 1, wherein the first edge and the second edge define an included angle of approximately 2 degrees to approximately 160 degrees.

9. The tool of claim 8, wherein the at least one forward-facing intake orifice comprises three forward facing intake orifices.

10. The tool of claim 9, wherein each of the three forward-facing intake orifices are separated from each other by an angle of between approximately 15 degrees and approximately 60 degrees.

11. The tool of claim 1, further comprising a second shelf substantially the same as the first shelf and positioned on an opposing side of the suction head from the first shelf, the tool further comprising a second recess substantially the same as the first recess positioned in the top surface of the second shelf and a second upward-facing intake orifice substantially the same as the first upward-facing intake orifice extending through the bottom of the second recess.

12. The tool of claim 11, wherein the at least one forward-facing intake orifice comprises three forward facing intake orifices.

13. The tool of claim 12, wherein each of the three forward-facing intake orifices are separated from each other by an angle of between approximately 15 degrees and approximately 60 degrees.

14. The tool of claim 11, wherein the at least one forward-facing intake orifice comprises two forward facing intake orifices.

15. The tool of claim 14, wherein each of the two forward-facing intake orifices are separated from each other by an angle of between approximately 15 degrees and approximately 60 degrees.

* * * * *